United States Patent
Withagen et al.

(10) Patent No.: US 9,445,771 B2
(45) Date of Patent: Sep. 20, 2016

(54) REAL-TIME FEEDBACK FOR PREVENTING HIGH DOSE C-ARCH GEOMETRY POSITIONS

(71) Applicant: KONINKLIJKE PHILIPS N.V., Eindhoven (NL)

(72) Inventors: Petrus Johannes Withagen, Halsteren (NL); Markus Johannes Harmen Den Hartog, Eindhoven (NL); Bart Pierre Antoine Jozef Hoornaert, Arendonk (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 143 days.

(21) Appl. No.: 14/363,736

(22) PCT Filed: Dec. 5, 2012

(86) PCT No.: PCT/IB2012/056993
§ 371 (c)(1),
(2) Date: Jun. 6, 2014

(87) PCT Pub. No.: WO2013/088308
PCT Pub. Date: Jun. 20, 2013

(65) Prior Publication Data
US 2014/0307855 A1    Oct. 16, 2014

Related U.S. Application Data

(60) Provisional application No. 61/570,356, filed on Dec. 14, 2011, provisional application No. 61/661,404, filed on Jun. 19, 2012.

(51) Int. Cl.
*H05G 1/64* (2006.01)
*A61B 6/10* (2006.01)
(Continued)

(52) U.S. Cl.
CPC ............... *A61B 6/10* (2013.01); *A61B 6/461* (2013.01); *A61B 6/467* (2013.01); *A61B 6/5294* (2013.01);
(Continued)

(58) Field of Classification Search
CPC ...... H05G 1/046; A61B 6/10; A61B 6/5294; A61B 6/4441; A61B 6/503; A61B 6/461; A61B 6/467
USPC .......................................................... 378/98
See application file for complete search history.

(56) References Cited

U.S. PATENT DOCUMENTS

| | | |
|---|---|---|
| 7,463,715 B2 | 12/2008 | Spahn |
| 2008/0123920 A1* | 5/2008 | Toth ........................ A61B 6/032 |
| | | 382/131 |

(Continued)

FOREIGN PATENT DOCUMENTS

| | | |
|---|---|---|
| DE | 102008028929 A1 | 12/2009 |
| DE | 102008047811 | 4/2010 |

(Continued)

OTHER PUBLICATIONS

C.W. Hamm, et al., "Diagnostische Herzkatheteruntersuchung", Clinical Research in Cardiology, Steinkopff-Verlag, DA, vol. 97, No. 8, Aug. 22, 2008, pp. 483-488.

(Continued)

*Primary Examiner* — Courtney Thomas

(57) ABSTRACT

An apparatus aids operation of an interventional x-ray imager during image acquisition, where the X-ray imager is configured to vary X-ray dosages depending on differences in X-ray attenuation levels across an object of interest to be imaged. The X-ray imager is further configured to assume any one of a plurality of imaging geometry positions when acquiring an image. An indication, visual, acoustic or haptic, to the operator of the X-ray imager is provided on the incurred change in X-ray dosage when changing from a current projection view to an updated projection view, while a given constant image quality is maintained throughout the different views.

23 Claims, 7 Drawing Sheets

(51) Int. Cl.
  *G06F 19/00* (2011.01)
  *A61B 6/00* (2006.01)
(52) U.S. Cl.
  CPC ........... *A61B 6/542* (2013.01); *G06F 19/3406* (2013.01); *A61B 6/4441* (2013.01); *A61B 6/503* (2013.01)

(56) References Cited

U.S. PATENT DOCUMENTS

| | | |
|---|---|---|
| 2009/0022275 A1 | 1/2009 | Grebner et al. |
| 2011/0019791 A1 | 1/2011 | Mueller |
| 2013/0251106 A1* | 9/2013 | Tajima .................... H05G 1/44 378/62 |

FOREIGN PATENT DOCUMENTS

| | | |
|---|---|---|
| DE | 102008049565 | 4/2010 |
| WO | WO2011042834 | 4/2011 |

OTHER PUBLICATIONS

E. Kuon, et al., "Identification of Less-Irradiating Tube Angulations in Invasive Cardiology", Journal of the American College of Cardiology, Elsevier, New York, NY US, vol. 44, No. 7, Oct. 6, 2004, whole document.

I.R. Smith, et al., "Measures of Radiation Exposure in Cardiac Imaging and the Impact of Case Complexity", Heart, Lung and Circulation, Elsevier, Amsterdam, NL, vol. 17. No. 3, Jun. 1, 2008, pp. 224-231.

* cited by examiner

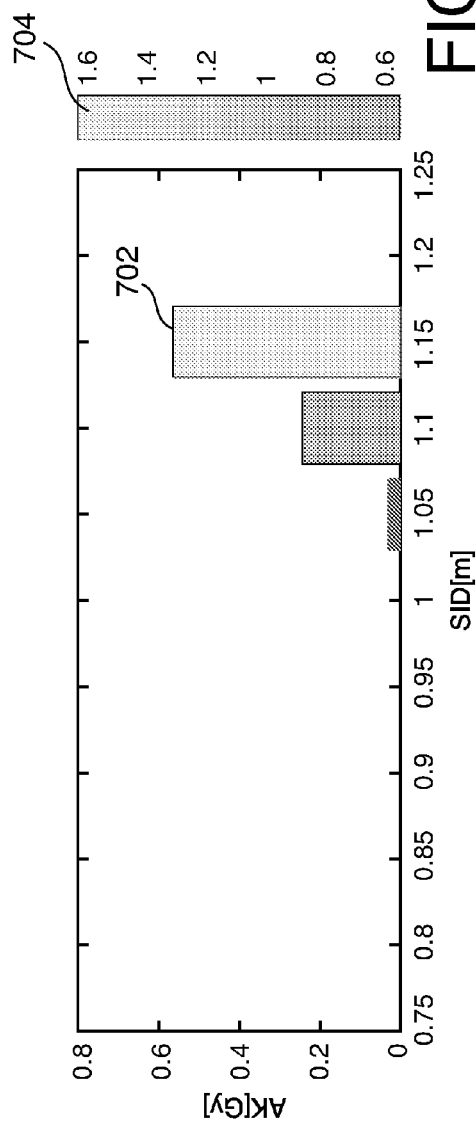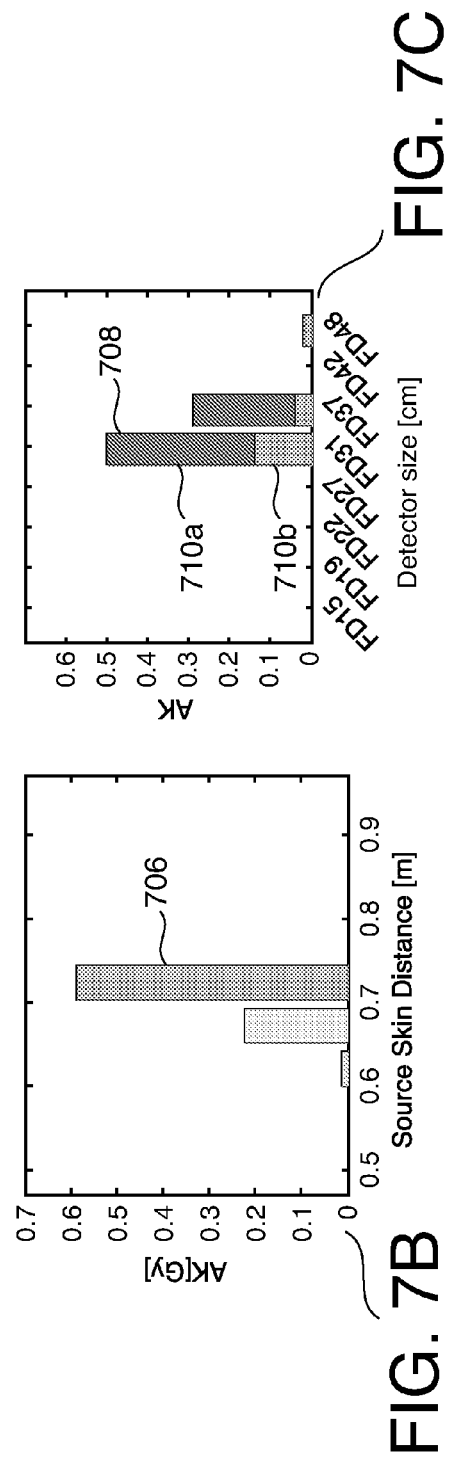

REAL-TIME FEEDBACK FOR PREVENTING HIGH DOSE C-ARCH GEOMETRY POSITIONS

CROSS-REFERENCE TO PRIOR APPLICATIONS

This application is the U.S. National Phase application under 35 U.S.C. §371 of International Application Serial No. PCT/IB2012/056993, filed on Dec. 5, 2012, which claims the benefit of U.S. Applications Ser. Nos. 61/661,404, filed on Jun. 19, 2012 and 61/570,356, filed on Dec. 14, 2011. These applications are hereby incorporated by reference herein.

FIELD OF THE INVENTION

The present invention relates to an apparatus for aiding operation of an interventional x-ray imager during image acquisition, to a method of aiding operation of an x-ray imager, to an interventional x-ray imager, to a computer program element and to a computer readable medium.

BACKGROUND OF THE INVENTION

X-ray imaging equipment is widely used by medical personnel to gain clues about a patient's condition or during medical interventions. WO 2011/042834 discloses X-ray imaging equipment.

When using the X-ray equipment, the patient is inevitably exposed to some X-ray radiation which poses a health risk. Modern X-ray equipment allows the operator to vary the X-ray dosage according to the medical need at hand. This freedom however may turn into a burden on medical personal desirous to strike the right balance between the level of patient's X-ray exposure used in a given image acquisition and the medical relevance of the image material obtained during that acquisition.

SUMMARY OF THE INVENTION

There may therefore be a need to support medical practitioners when operating x-ray imagers.

The object of the present invention is solved by the subject matter of the independent claims wherein further embodiments are incorporated in the dependent claims.

It should be noted that the following described aspects of the invention are equally applicable to the method of aiding operation of an intervention x-ray imager during image acquisition, to the x-ray imager, to the computer program element, and to the computer readable medium.

According to one aspect of the invention there is provided apparatus for aiding operation of an x-ray imager during an image acquisition procedure.

The X-ray imager is capable of varying X-ray dosages depending on differences in X-ray attenuation levels across an object of interest to be imaged and is capable of assuming any one of a plurality of imaging geometry positions when acquiring an image.

The apparatus comprises:

an input unit configured to receive a request to change a current imaging geometry position for an updated imaging geometry position for use in the image acquisition;

a memory unit configured to store a functional relationship between the imaging geometry positions and the X-ray dosages, the functional relationship based on expected X-ray attenuation levels in the object of interest;

an output unit configured to use the stored functional relationship to provide to a human operator of the interventional X-ray imager an indication of the change in X-ray dosage required at the updated imaging geometry position relative to the X-ray dosage required at the a reference position.

An imaging acquisition procedure includes one or more "runs" in each of which a respective imaging geometry position is used for an exposure or to "shoot" or acquire for example an X-ray projection image.

According to one embodiment, the X-ray imager is of the interventional C-arm type with manual controls to change the imaging geometry positions. Imaging geometry positions are coordinates or other setting parameters for the imager's movable one or more parts. The combined mutual spatial relationship between those parts and the position of the object to be imaged define the angle of incidence used for the image acquisition. The imager includes an X-ray source and a detector for detecting X-rays emitted by the source and attenuated by the object to be imaged. The angle of incidence of a "clinical" or projection view defines the angle in 3D space at which the X-ray is incident on the object.

According to one embodiment the imaging geometry position is given by a parameter comprising any one or more of a rotation angle and an angulation angle of a C-arm and a selectable X-ray source-to-image detector distance (SID).

In interventional C-Arch X-ray imaging, some imaging geometry positions or angles are far more patient "X-ray dosage friendly" than others so less dosage is required. This dosage required to maintain a desired image quality is directly correlated with the distance travel of the X-ray in the tissue. For instance, in a cardiac application, a "high angle" spider view requires up to 6 times the X-ray dose than for a normal frontal (AP—anterior-posterior) image. The apparatus harnesses the fact that relatively minor variations of the geometry angle have little impact on the visibility of the anatomy but can have a major reductive impact on the dose.

In a clinical sense optimal view may require a relatively high dosage, but a slightly different angle off this optimal view may be just as good in terms of image quality and anatomic view, but still require a far lower X-ray dosage.

According to one embodiment the image quality to be maintained across the different positions is variable. The data values held in memory are then recalculated. This gives the clinician more control when choosing a suitable view.

The functional relationship is a set of data values describing how the required dosage changes with a change in imaging geometry positions. The values describe this change relative to the required X-ray dosage at a selectable reference imaging geometry position. Each possible imaging geometry position coordinate is associated with a ratio describing the relative change in required dosage at that coordinate position. In one embodiment, it is only a selectable subset of all possible imaging geometry position coordinates ("phase space") that have those ratios assigned. The ratios for intermediate positions can then be produced on demand by an interpolation routine The apparatus aids the physician chose the best compromise between viewing angle and patient dose. Physicians unaware of both the current geometry angle and the SID setting may use a higher angle/SID for viewing than may be necessary. This is especially the case when the operator overshoots the desired geometry position when using the imager's manual imaging geometry position controls and does not correct for this.

The indication signal generated (in real-time) by the apparatus is intuitive to allow the clinician even in a very busy environment such as during an intervention to quickly ascertain how the dosage requirement would change with varying imaging geometry position. He or she can quickly tell whether or not the required dosage at an envisaged position is high dosage or not and how the dosage changes in a neighborhood around that envisaged position to so find a position sufficiently close nearby but with possibly lower dosage requirements.

According to one embodiment the indication is visual and displayable on a screen as a graphics display, the graphics display when so displayed including a plurality of geometry position versus X-ray dosage indicator elements, each indicator element representing one of the geometry positions and the relative change of X-ray dosage required at that imaging geometry position.

According to one embodiment the change in X-ray dosage is color-coded by the indicator elements, the color-coding directly varying with the relative changes in X-ray dosage requirements across the indicator elements.

According to one embodiment the indicator elements form points of one of a plurality of contour lines of the stored functional relationship between imaging geometry positions and X-ray dosages. Intuitively, the contour line GUI forms a "virtual landscape" of the functional relationship between required dosage levels and imaging geometry positions.

According to one embodiment the graphics display is a graphical user interface including a cursor, the position of the cursor in the graphics display representative of the current imaging geometry position, the cursor position varying as the X-ray imager changes from the current position to the updated imaging geometry position.

Controlling the geometry position remains with the operator but the apparatus raises and maintains awareness of this view-versus-dosage tradeoff and provides an intuitive visual clue by way of the GUI to better navigate the "virtual landscape" of this functional relationship. In this way ALRA guidelines can be observed even during stressful interventions.

According to one embodiment the indication is visual and displayable on a screen as a graphics display, the graphics display when so displayed including a grid structure with different grid position indicators representative of different imaging geometry positions. The grid position indicators are visually coded with the coding varying across the grid position indicators with the change in required X-ray dosage, said change expressed in terms of the level of X-ray attenuation to be expected when the respective imaging geometry is used for the image acquisition of the object. The graphics display further includes at least one dosage usage indicator having a size and is positioned at any one of the grid points. Said size changes with the X-ray dosage used in a current imaging procedure or in a series of previous imaging procedures at the respective imaging geometry position.

According to one embodiment, the graphics display includes a further dosage usage indicator having a size, the output unit operative to scale the two sizes relative to one another so that the larger one of the two sizes is not to exceed a predefined maximum size, the maximum size preset in relation to a size of the displayed grid. This prevents the size of the dosage usage indictors to grow out of proportion relative to the other indicators which otherwise may block the view on the grid. This is useful in particular where one particular geometry position is used disproportionately more frequently than others.

According to one embodiment the level of attenuation is visualized in terms of any one of i) average water equivalent patient thickness, ii) average or peak air Kerma rate, or iii) effective dosage for the object. According to one embodiment, the amount or level of attenuation in a patient using a given imaging geometry is mapped into a scale of water equivalent in-tissue path length. For bone for example, 1 cm of bone will result in several cm of water equivalent patient thickness.

The generated graphics display allows representing difficult to visualize 4-dimentional information on a 2D screen by making use, in one embodiment, of color-coding and indicator symbols of different sizes. The GUI allows simultaneous display of both exam-usage (number of frames, number of runs, run time or dose/AK) and average patient thickness or relative dose as a function of angulation and rotation of the C-arm in the imager system. Because of the simultaneous display of patient thickness and exam dosage usage, it is possible for the operator to maintain a complete overview of how dosage has been used either in the current exam or in a previous series of exams carried out on the object. This graphics information is retrievable and viewable in an off-line environment after the actual imaging procedure and may provide benefits training and education purposes for X-ray imager operators to gain a better understanding of dosage usage expressed in terms of different quantities and parameters.

According to one embodiment the indication is visual and displayable on a screen as a graphics display, the object disposed on a table during the image acquisition, the graphics display when so displayed including a color-coded Source-Image-Distance or table height indicator, the color coding indicating the relative change in X-ray dosage required for the respective Source-Image-Distance or table height.

According to one embodiment the indication is visual and displayable on a screen as a graphics display, the graphics display when so displayed including a visually-coded indicator for the x-ray dosage used for a user-selectable detector size in the imaging procedure and a collimation usage indicator indicating collimator usage for said selected detector surface size.

The so generated graphical information on X-ray dosage may also be used by reporting tools to better review the exam history for a specific patient and or operator or may be sued "online" and are updated accordingly as the imaging procedure progresses.

According to one embodiment the indication is provided by an acoustical signal having a pitch in direct variance with the relative change in X-ray dosage requirements across the plurality of imaging geometry positions, the pitch so varying as the imaging geometry position changes from the current imaging geometry position to the updated imaging geometry position.

In one embodiment the indication signal is provided as a negative feedback signal to the operator of the C-arm imager whilst controlling the position using a joystick.

The negative feedback mechanism of the geometry movement controls favor low dose angles and discourage the operator to use high dose angles by guiding him or her away from high dose angles and towards low dose angles.

According to one embodiment the (real-time) negative feedback indication signal acts on a mechanical control device, such as a joystick, used by the operator to request the change in imaging geometry position.

According to one embodiment the negative feedback is in the form of vibrations imparted on the mechanical control device.

The strength of the negative feedback or the frequency of the vibrations is in direct variance with the relative change in X-ray dosage requirements at and across the plurality of imaging geometry positions. The feedback strength such as the frequency varies as the imaging geometry position changes from the current position to the updated imaging geometry position. In this embodiment, the joystick vibrates at a higher frequency as the imager's c-arm moves from position to position with higher x-ray dosage demands.

According to one embodiment, negative feedback is by adapting the speed with which the c-arm moves across the different imaging geometry positions. Motions toward high dosage angels are decelerated whereas motions towards low dosage angles are accelerated to so encourage the operator to choose low dosage angles.

The apparatus delivers negative feedback in the sense that low dosage areas in the phase space formed by all possible imaging geometry positions are considered "stable states" whereas high dosage areas are considered by the apparatus control circuitry as "perturbed states". The apparatus acts on the control device to oppose change of imaging geometry position away from the stable sates and favors changes towards stable states.

The apparatus can be used with any X-ray imager with manual geometry movement controls. The apparatus can be integrated as an add-on into an existing imaging geometry movement system. In one embodiment it forms an extension of a collision prevention subsystem which avoids moving parts to hit objects that happen to come its way. The graphical user interface can be presented on the native monitors in use in an existing X-ray imager.

BRIEF DESCRIPTION OF THE DRAWINGS

Exemplary embodiments of the invention will now be described with reference to the following drawings wherein:

FIG. 7A-7C show further embodiments of a graphical user interface generated by the apparatus in FIG. 1.

DETAILED DESCRIPTION OF EMBODIMENTS

Figure 1:
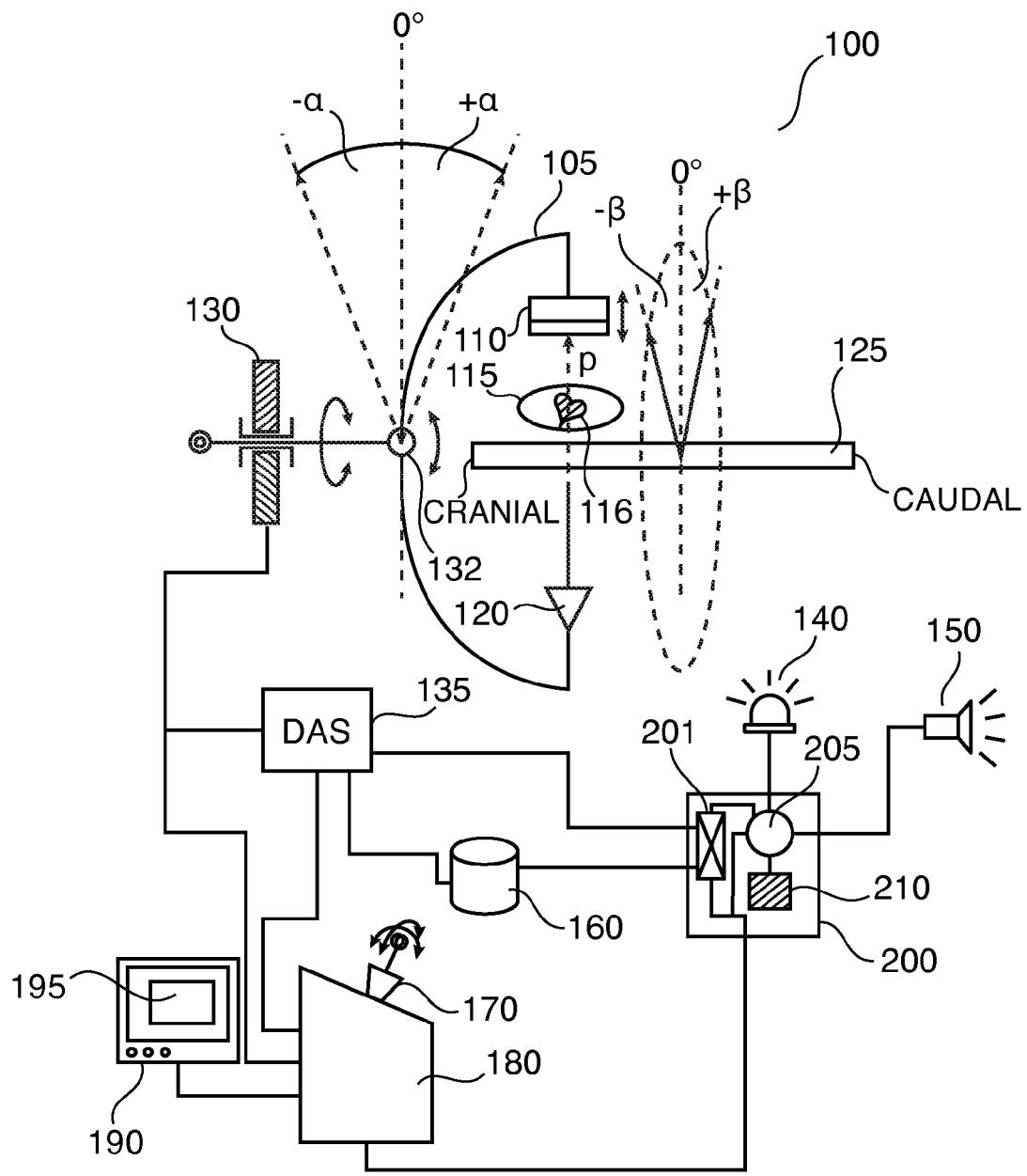
FIG. 1 shows a schematic block diagram of an x-ray imager in co-operation with an apparatus for aiding operation of the x-ray imager.

With reference to FIG. 1, an interventional x-ray imaging equipment 100 (X-ray imager) of the C-arm type is shown. A "C" shaped arm 105 or fame has attached to one of its end an x-ray source 120 and in opposed relationship on the other end a detector 110 configured to detect x-rays emitted by said x-ray source 120.

Rigid C arm 105 is connected to a shaft by way of a joint. Shaft is journaled on a bearing 130 to allow rotation of arm 105 carrying with it the ensemble of X-ray source 120 and detector 105 ("source-detector ensemble"). Bearing 130 includes a slip ring arrangement so that electronic signals between the source-detector ensemble and an operator console 180 can be exchanged via a suitable communication network.

A table or patient stretcher 125 is arranged centrally between a circle swept out by x-ray source 120 and detector 105 whilst arm 105 is rotating. A patient 115 is disposed on table 125 such that an anatomical object of interest is arranged substantially in the center of said circle. The object of interest may be a patient's heart during a cardiac intervention supported by the X-ray imager, for example when positioning a catheter in a cardiac vessel.

During an image acquisition run, patient 115 lies on the table 125 having patient's head pointing towards the cranial direction and the patient's feet towards the caudal direction as indicated in FIG. 1. C-arm 105 rotates around the patient 115 and thus heart 116 to assume a specific angular position $\beta$ to so enable a desired projection view on heart 116 at which an X-ray image is to be acquired.

X-ray source 120 then emits X-rays impacting on patient's heart 116. The X-rays pass from source 120 through the heart 116 and are then incident on detector 110. Each x-ray p impinges on detector 120 and generates a signal which is translated by data acquisition system 135 into pixel image information. X-ray p is attenuated as it passes through heart 116 tissue. The degree or level of attenuation is recorded and encoded as a respective gray value associated with that pixel.

Because C-arm 105 is rotatable around heart 116 and a longitudinal axis of patient 115, a plurality of projection images ("views") at a number of different projection angles $-\beta$ or $+\beta$ beta can be acquired as desired by the operator of imager 100.

Imager 100 affords a further degree of freedom, namely rotation ("angulation") around joint 132 and an axis perpendicular to the longitudinal axis. So the plane of the circle swept out by the rotatable source-detector ensemble carried by C-arm 105 can be tilted around joint 132 at a desired angulation angle $-\alpha/+\alpha$ with respect to a reference direction $0°$. At $0°$ angulation the source-detector line is approximately normal to patient's chest. An angulation by $+\alpha$ would tilt arm 105 so that detector 110 is moved in caudal direction whereas angulation by $-\alpha$ would tilt arm 105 so that detector 110 is moved in cranial direction.

A plurality of projection images acquired at different angulation and rotation angles combinations are then forwarded from DAS 135 to a database 160 where the projection images are stored in a suitable format such as DICOM. Operation of x-ray imager 100 is controlled at operation console 180. Operation console 180 is in communication with a screen 190 where the acquired projection images may be viewed.

In the x-ray imager 100, a projection angle (angle of incidence) or "clinical" view" is defined by the pair of rotation and angulation angles $(\alpha, \beta)$ and is chosen by operator depending on the medical diagnostic or interventional task at hand.

A yet further degree of freedom is provided by a radial movability of detector 110 as indicated by the vertical double arrow in FIG. 1. Detector 110 is moveable towards or away from patient 115. This allows controlling scatter when impacting X-rays are egressing body tissue.

X-ray imager 100 may also include an automatic X-ray dosage control loop unit (not shown) ensuring that the pre-set maximum of allowable x-ray dosage for the patient 115 is observed.

X-ray dosage controller also controls entrance X-ray dosage as emitted by X-ray source 120 to so control the image quality (IQ) which can be quantified and output as a ratio number by a suitably configured contrast-to-noise (CNR) circuitry upon reading in the pixel information in the projection image. IQ varies directly with the X-ray dosage so that acquiring the image using a higher X-ray dosage would increase the IQ of that image.

So the two aspects of X-ray image acquisitions are (i) the projection angle which determines which part of the anatomy may be, in principle, represented in the image and (ii) the X-ray dosage used for the acquisition which determines the image quality in which the anatomy is represented.

Figure 2:
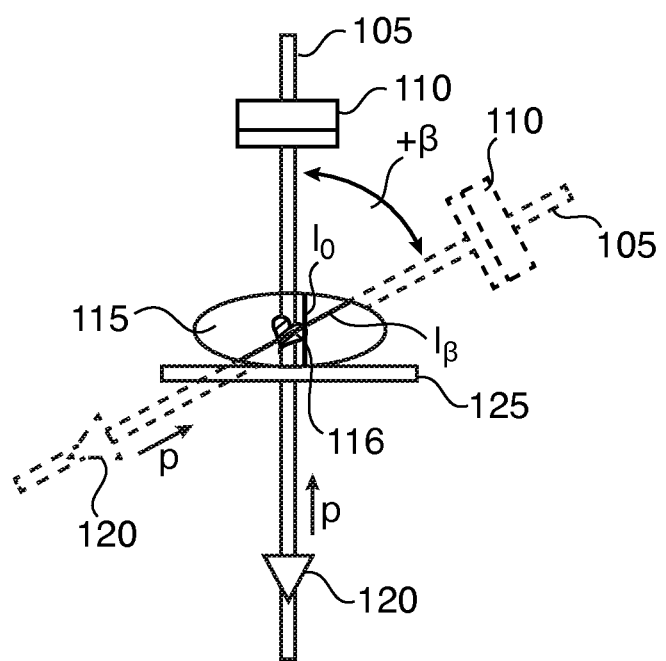
FIG. 2 schematically shows a front elevation view on the imager in FIG. 1 during image acquisition.

There is a functional relationship between the projection angle and the required X-ray dosage and the physics underlying this functional relationship is now explained with reference to FIG. 2 showing a front elevation view of imager 100.

The solid vertical line representation of C arm 105 is shown in 0° position so sensor-detector line is about perpendicular to patient 115's chest. The dotted line representation shows C-arm 105 at rotation angle $+\beta>0°$.

In both angular positions, X-ray p emitted by x-ray source 120 is attenuated as it passes through patient 115's heart 116 and the so attenuated X-ray p is then detected by the detector 110. Because of the anatomy of the heart 116 and patient 115's chest, at rotation angle 0° the in-tissue path length $l_0$ is shorter than the in-tissue path length $l_\beta$ at rotation angle $+\beta$. FIG. 2 shows exemplary, that changing the angle of incidence is in general accompanied by a change of the in-tissue path length, that is, the amount of tissue that need be penetrated by the x-ray when entering the tissue at that angle of incidence. The Beer-Lambert law states that the X-ray intensity drop as detected at detector 110 is exponentially proportional to the in-tissue path length. In other words, the entrance X-ray dose (the dosage required before the x-ray penetrates the tissue) needed for rotation angle $+\beta$ ("high angle") is exponentially greater than the entrance X-ray dosage needed at 0° rotation angle for the anterior-posterior (AP) image, given that in both cases the same egress X-ray dosage (the dosage detectable by detector 110) is required to so maintain a pre-set IQ. A similar observation holds true by analogy for angulation angles $\alpha$.

The inverse square law for radiation propagation states that the dosage decreases with the inverse square of the total distance travelled by the X-ray, so a similar analysis can be done when the Source Image Distance (SID) is changed.

It has been observed that approximately for every 3 cm of additional tissue (normalized to equivalent water thickness), the patient entrance X-ray dosage will need be increased with a factor of 2 to maintain the same CNR or the CNR will drop by a factor of $\sqrt{2}$ if the X-ray dosage remains unchanged. In practice, a "high angle" view will even require more than 4-6 the dosage to maintain the CNR or the CNR will drop by a factor of 2-3 if the X-ray dosage remains unchanged.

Projection angle or view ($\alpha$, $\beta$), along with the SID given by the selectable radial position of detector 110 together define an imaging geometry position ($\alpha$, $\beta$, SID). The imaging geometry position determines which anatomical feature or which part of the anatomy of interest may be visible in a projection image.

The imaging geometry position co-ordinates ($\alpha$, $\beta$, SID) are selected by the operator at the operator console 180 using a mechanical control device such as joy-stick 170. For example moving the joy-stick to the left or to the right effects changing the angulation angle a cranially ($-\alpha$) or caudally ($+\alpha$), respectively. Similarly, moving the joy-stick up or down effects changing the rotation angle $\beta$ clockwise ($+\beta$) or counter-clockwise ($-\beta$), respectively. The SID, that is the radial position of detector 110, may be adjusted by pulling or pushing of joystick 170.

Although a change in the imaging geometry position (other than the SID) in and of itself will not change the dosage levels, the differences in attenuation levels associated with such a geometry change in general will. As shown above at FIG. 2, this is because the longer in-tissue path length the higher the required X-ray dosage to so maintain the pre-set image quality demands.

Referring again to FIG. 1, the lower right of which shows a diagrammatic block diagram of an apparatus for aiding operation of the interventional x-ray imager 100.

Apparatus 200, a digital processing unit, comprises an input unit 201, a memory unit 205, and an output unit 210.

The components of the apparatus are shown incorporated in processing unit 200. However, this is for clarity of illustration only. The apparatus components input unit 201, a memory unit 205, and an output unit 210 may be instead distributed and connected in a suitable communication network. In the embodiment shown in FIG. 1, components 201, 201 and 205 are running as software routines on the processing unit 200. The components may be programmed in a suitable scientific computing platform such as Matlab® or Simulink® and then translated into C++ or C routines maintained in a library and linked when called on by processing unit 200. In yet other embodiments, the components may also be arranged as dedicated FPGAs or as hardwired standalone chips.

Broadly speaking, the apparatus 200 helps the operating physician in the intervention procedure to negotiate the trade-off between the best clinical view on the heart 116 and the lowest possible x-ray exposure for the patient 115. As mentioned earlier the clinical view is determined by the chosen imaging geometry position. Some geometry positions (high angles) provide, from a clinical perspective, the best view of the anatomy. However this may come at a price of a high x-ray dosage exposure of the patient. Using an imaging geometry position slightly off that "a priori" best clinical view may deliver just about the same clinical view on the heart 116 but at a much lower x-ray dosage. Apparatus 200 aids the physician in operation of the image 100 by providing an indication of this this dosage versus geometry position trade-off.

Indication is delivered visually by way of a user interface 195 displayable on the screen 119 during an intervention or exam or by other visual clues such as warning light 140 flashing or changing color as the c-arm imaging geometry position approaches a high dosage angle. Instead or in addition to the visual indication, a speaker 150 may be actuated by a suitably configured sound card to give off a warning tone having its pitch in direct variance as C arm 105 approaches any high dosage angle areas in the phase space formed by all possible image geometry positions.

In another embodiment apparatus 200 is configured to deliver a haptic indication in the form of a negative feedback on the joy-stick 170 when used by the operator to change the imaging geometry positions of C-arm 105 and steer towards high dosage angle areas.

In one embodiment, vibration of the joy-stick is effected by suitably configured actuator as the c-arm imaging geometry position approaches a high dosage angle. The frequency of the vibration becomes higher as the high dosage angle is approached thereby warning the operator accordingly.

In another embodiment, if joystick 170 is operated so that c-arm 105 moves towards high dosage angles, movability of joystick is automatically impeded thereby discouraging the operator to pursue that direction toward high dosage angular areas.

In either of the above haptic examples of negative feedback, the joystick is arranged in force feedback technology. A pair of electro-motors is arranged in the joystick housing. The electro-motors are controlled by a joystick-built in processor in communication with apparatus 200. Depending on the currently required X-ray dosage levels, control commands are issued by apparatus 200 to joystick processor. The motors are configured to engage via a gear train the part of the joystick shaft extending into the housing thereby imparting motion on the shaft. The motors produce a mechanical moment to progressively counteract user imparted joystick shaft motion, when the user imparted joystick shaft motion would result in c-arm 105 assuming geometry position with increasing x-ray dosage requirements.

Operation

Apparatus 200 aims to predict how much the dose levels would increase or decrease when changing the imaging geometry position or settings.

The expected change in X-ray dosage values versus the imaging geometry positions (relative to a reference imaging geometry position), are preloaded (before the exam) into the memory 110 in a suitable data structure, such as a two or higher dimensional matrix or an array.

In one embodiment, averages from previous interventions are used to build up the relative change in X-ray dosage values to represent the functional relationship between expected X-ray dosage levels at each of the possible imaging geometry positions. To this end, for each of the possible imaging geometry, entrance and egress dosages are compared and their ratio recorded. In this way over the course of time, stockpile of data pair values can be built up representing a sample of the functional relationship. In the alternative, a phantom may be uses to obtain the desired dosage-imaging position data value pairs in a number of X-ray test runs on the phantom.

In on embodiment a physical and/or mathematical model of the relevant anatomy is used to reconstruct this functional relationship and can then be used by apparatus 200 to predict the expected attenuation levels and hence the required X-ray dosage at each of the possible imaging geometry positions and image configurations.

To generate the values representing this functional relationship, cardiac cross-sectional images can be obtained by a CT scanner and a 3D geometric mesh mimicking the geometric shape of the heart and the surrounding chest tissue can be so established. Preferably the mesh width corresponds to the angular resolution capabilities (in terms of fractions of angular increments) at which C-arm 105 actuator operates to effect rotation and angulation motion. For each 3D mesh voxel, an X-radiation absorption or attenuation coefficient can be assigned because the chemical composition of the heart and surrounding tissue is well understood. Using the Lambert-Beer law and the inverse square law introduced above, an expected attenuation level for each direction at the predefined angular increments as will be used by the imager 100's c-arm actuator can then be calculated in a loop cycling through each of the possible projection directions.

In a further embodiment it is envisaged to store a "catalogue" of different functional relationships, each corresponding to a patient's sex, height, weight etc., to so better account for the different physiques of patients that may come to be imaged. As shown in FIG. 2, it is to a substantial extent the configuration of the body tissue surrounding the heart that accounts for much of the attenuations of the impacting X-rays, a more corpulent patient attracting higher attenuation levels than an average stature patient.

The so calculated expected change in attenuation levels relative to a defined reference position is then recorded in a tabular or matrix structure and is then pre-loaded in memory 205. Apparatus 200 is then operational.

Once imager 100 is started up and patient 115 is ready for examination, the operator uses joystick 170 to have imager 100 assume a targeted imaging geometry position. Low level control signals issued by joystick 170 are translated by console 180 into higher level data packets according to a protocol and dispatched across a communication network via slip ring to actuators (for example servo-motors) arranged around c-arm 105. Actuators' interfaces than translate the received data packets into control signals and the actuators set c-arm 105 into motion. C-arm 105 is then moving in increments from an initial position to the operator requested target position across a plurality of intermediate positions. A log record of the continuously updated intermediate positions is transmitted from actuators back to operator console 180 from which it is relayed to apparatus 200 and received at input interface 201.

Apparatus 200 is therefore aware of any current imaging position of c-arm 105.

The received imaging positions are then compared against the data values stored in memory 205, the data values representing the previously described relationship between expected X-ray dosage values versus imaging geometry positions. Processor 200 then uses the matrix to look-up the expected relative change in X-ray dosage for each of the intermediate positions.

Apparatus 200 achieves its aiding functionality by generating an indication to the operator based on each of the currently looked-up expected relative change in X-ray dosage as c-arm 105 passes through the intermediate positions towards the requested updated or target imaging geometry position.

As indicted earlier, the indication signal generated by apparatus 200 is either visual, acoustic or haptic or a combination of all or some of the previous.

Apart from operating warning light 140, speaker 150 or delivering the negative feedback signal to joystick 170 as explained above, apparatus is configured to generate a further or alternative visual indication in the form of a graphical user interface 195 displayable on screen 190 when imager 100 is in operation during an x-ray supported intervention.

Figure 3:
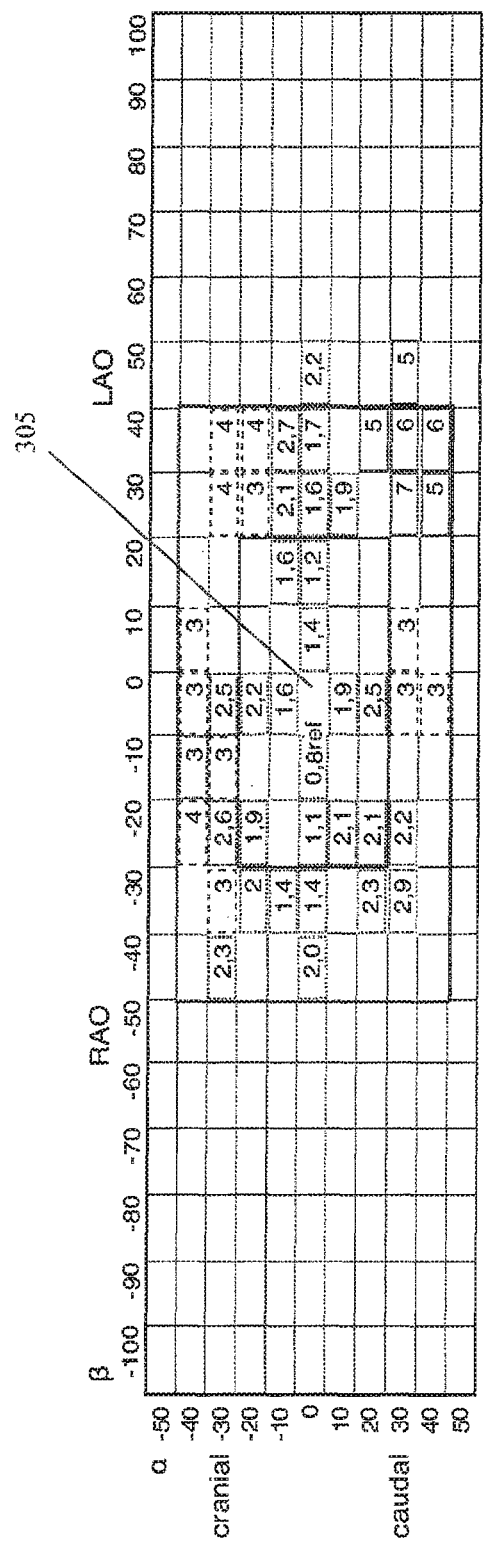
FIG. 3 shows one embodiment of a graphical user interface generated by the apparatus in FIG. 1.

With reference to FIG. 3, a schematic screenshot of a graphical user interface 195 according to one embodiment is shown. According to this embodiment, graphical user interface GUI 195 is generated as a matrix structure.

Each matrix entry is represented by a rectangular indicator element 301a-c,e each defined by its rows and column position and representative of the relative increase in x-ray dosage relative to dosage required at the reference imaging geometry position shown at as the centre (AP view, $\alpha=0°$, $\beta=0°$) matrix entry.

Matrix rows designate angulation $-\alpha$ (cranial)/$+\alpha$ (caudal), and matrix columns designate rotation angle $-\beta$ (Right Anterior Oblique RAO)/$+\beta$ (Left Anterior Oblique LAO). As an example, the entry $\alpha=-20°$ cranial/$\beta=-30°$ RAO means that at this imaging geometry position, in order to maintain the same IQ as at the reference position 305, an X-ray dosage twice the dosage as used at the reference position 305 is required. So across all matrix entries, the IQ is maintained (as measured by CNR) and the necessary adjustment to the entrance X-ray dosage delivered by source 120 is provided by imager 100's built-in automatic doses controller.

The value is either shown as a number and/or is colour coded by displaying the respective indicator elements 301a-c in a colour according to a colour palette to which the in-memory stored X-ray dosage values have been mapped by a GUI controller in communication with processor 200. The colour coding is schematically shown in FIG. 3 as different line styles used for the rectangular indicator elements 301a-c, ranging from solids lines for high dosage angles, dashed lines for middle dosage angles and dotted lines for low dosage angles. Coding by lines style instead of by colours may be used if a monochrome display or representation is used or desired when displaying GUI 195.

Indicator elements 301 a-c are shown inside a focus rectangle defined by RAO −50° to LAO +40°/cranial −40° to caudal −40°. Focus rectangle shows the range of all possible geometry imaging positions relevant for a particular intervention. Apparatus 200 provides the functionality to the user for selecting imaging geometry position ranges and GUI 195 is then updated accordingly, that is, focus rectangle is made larger or smaller, accordingly.

Indicator elements 301a-c inside the focus rectangle shown as blank indicate imaging geometry positions where the required X-ray dosage is similar to the one at reference AP position 305.

One example of a projection view often used by cardio clinicians is the "spider view" at LAO (left Anterior Oblique) 40°-50°/Caudal 25°-40°. It is believed that this range of angles affords a good view on the left main bifurcation (LM) in the coronary vessel network. This may be of relevance when navigating a balloon catheter to this vascular bifurcation to treat a stenosis. However, in some clinical environments that strictly police ALARA ("As Low As Reasonably Achievable") safety guidelines, no spider view is allowed because of the relatively high X-ray dosage required. For a spider view, angulation need be set to very high angles because the X-ray will need to pass nearly across the whole of patient's longitudinal axis and along the main artery to realize the spider view which translates into a very long in-tissue path and therefore high X-ray dosage to maintain IQ.

However, using GUI 195 as generated by apparatus 200 as proposed herein, a feasible ALARA compliant compromise may be negotiated: rather than insisting on the exact spider view angle ranges, the clinician would immediately learn from GUI 195 that a geometry position at LAO 30°/caudal 10° is reasonably close to the spider view but comes with the benefit of a mere 1.9 rise in X-ray dosage as compared to the dosage requirement 5-7 times the reference dosage had the clinician chosen to select an imaging geometry that squarely falls into the "dogmatic" spider view range specified above. In this way, apparatus 200 helps to still generate images of clinical relevance but at lower X-ray exposure. In the above spider view example, GUI 195 helped downing patient's exposure by between 30-50%.

According to one embodiment the reference position 305 can be selected and the numbers and/or colour-coding indicated on each of the indicator elements 301a-c are then recalculated accordingly.

In one embodiment, GUI controller is configured to use the current imaging geometry position as received at input unit 201 to control a cursor 196 (not shown in FIG. 3) which moves across the screen and the GUI matrix in accordance with the change in imaging geometry position of c-arm 105 when requested by user using joy-stick 170. In one embodiment, the cursor may be implemented by having the corresponding one of the indicator elements 301a-c flash or change its colour to so indicate the current imaging geometry position.

Figure 4:
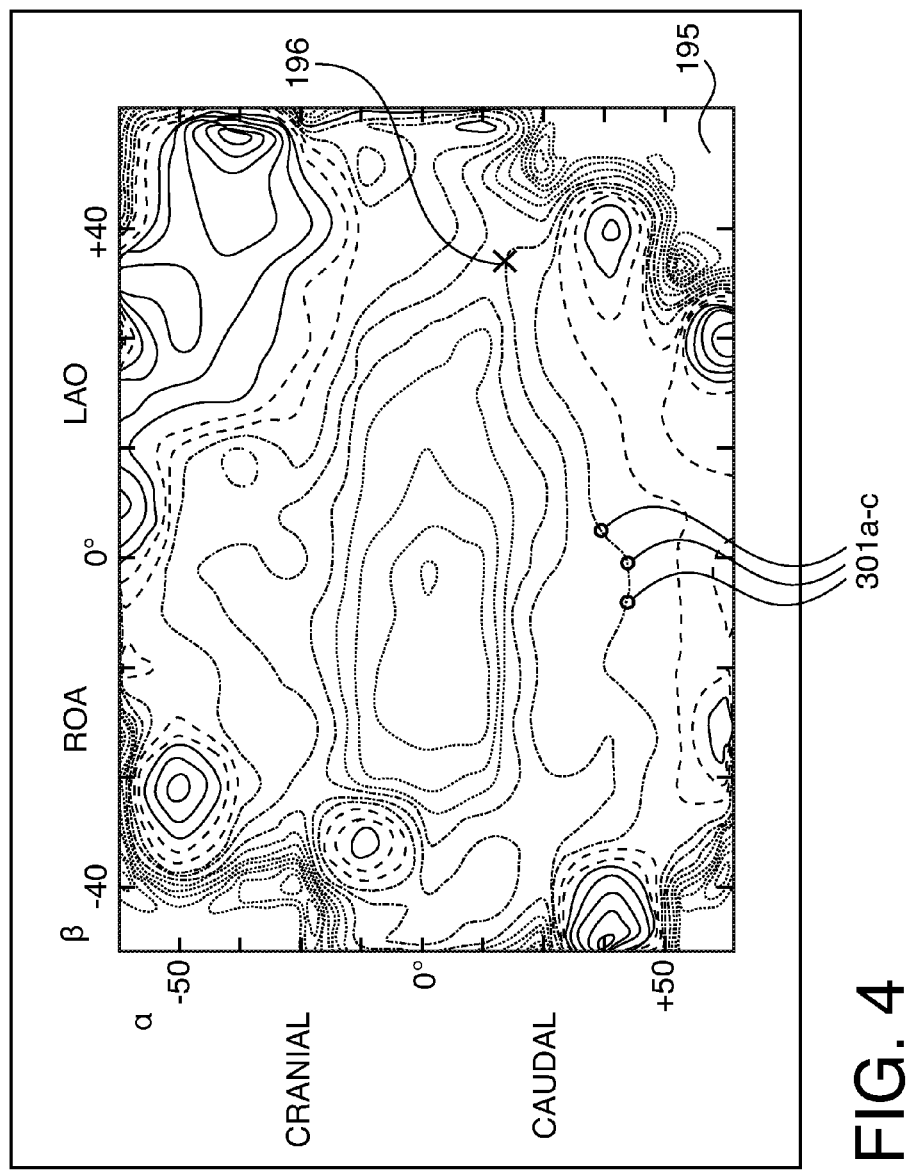
FIG. 4 shows a second embodiment of a graphical user interface generated by the apparatus in FIG. 1.

With reference to FIG. 4, a further schematic screenshot of the user interface 195 according to another embodiment is shown. In this embodiment, GUI controller is instructed by processor 200 to generate, based on the stored functional relationship between expected X-ray dosage levels and imaging geometry positions, a contour line of this functional relationship wherein the IQ across all imaging positions is maintained at a selectable constant value.

Figure 5:
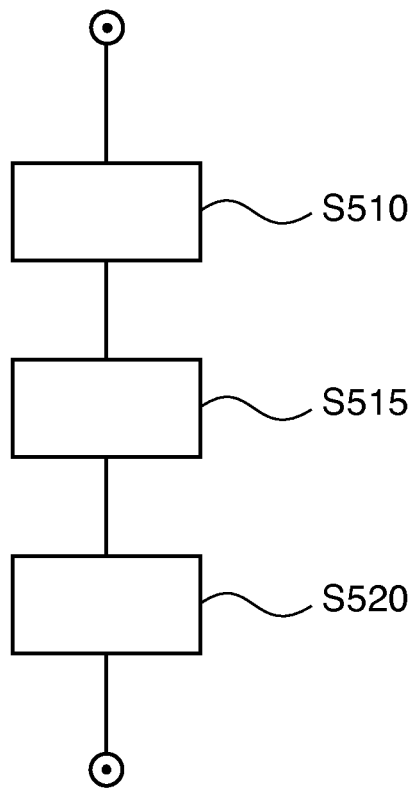
FIG. 5 shows a flow chart of a method of aiding operation of an x-ray imager.

Indicator elements 301 a-c now form points of different contour lines. Contour lines indicative of high dosage levels would be shown for example in red and lower levels of x-ray dosages would then be coded in colours ranging from yellow, orange, green down to blue. However it is understood that any other colour palette may be chosen. In FIG. 5, the colour coding is schematically represented by different line styles as has been done earlier in FIG. 4. Cursor position 196 indicates the current imaging geometry position assumed by C arm 105. Operating joy-stick 170 to request a change in imaging geometry position will effect cursor 196 to move across the GUI 195 in accord with the incrementally assumed intermediate positions until the requested final position is assumed by c-arm 105. Graphical user interface 195 therefore affords precise navigation across the different geometry positions and to stay clear from high level dosage angles.

In both FIGS. 3 and 4 it is assumed that image quality measured by the signal to noise ratio is assumed constant.

Figure 6:
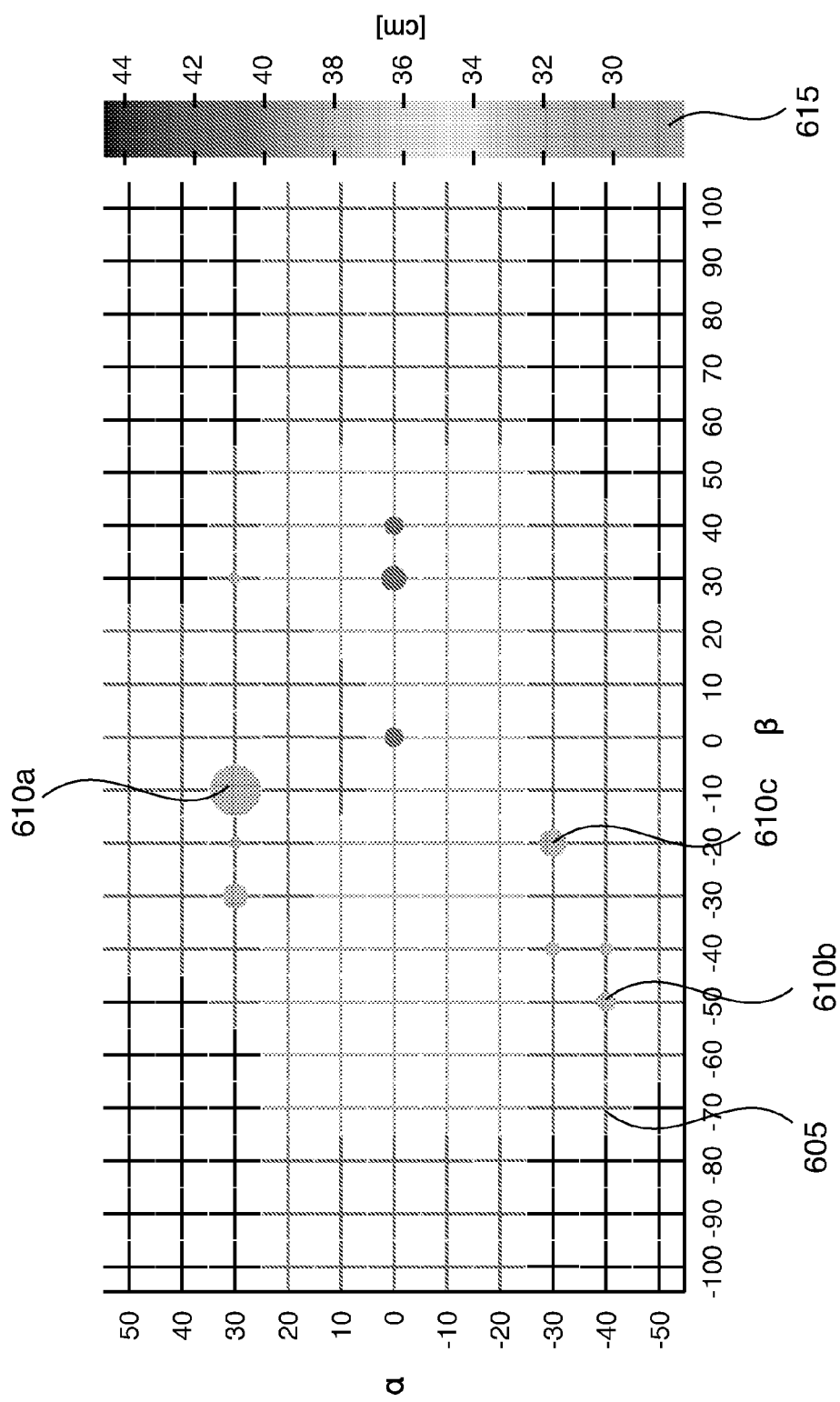
FIG. 6 shows a third embodiment of a graphical user interface generated by the apparatus in FIG. 1.

With reference to FIG. 6, a schematic screenshot of the user interface 195 according to another embodiment is shown. In this embodiment, GUI controller is instructed by processor 200 to generate a 2D angulation-rotation grid similar to the GUI in FIG. 3. In the embodiment of FIG. 6 however the grid points 605 are visually-coded to depict a relative patient thickness or effective dose that is to be expected when the respective imaging geometry (as indicted by that grid point) is used. In other words, patient thickness is displayed as a function of angulation and rotation. Visual coding is by color-, gray value -or line type or -line heaviness-coding as explained in more detail below and it is understood that same applies to the embodiments of FIGS. 3 and 4.

In the FIG. 6 embodiment, the visual coding is by gray-value coding so different shades of gray indicate the levels of attenuation or average patient thickness at the respective image geometry positions indicated by each of the grid points 605. For example in the gray-value coding in FIG. 6, the patient thickness at α=0°, β=30° is lower so the respective grid point is displayed in a darker grey shading than the actual or expected patient thickness at α=30°, β=−10° where the respective grid point is shown in lighter gray shade. In other embodiments the visual coding is by color coding so the color of individual grid points ranges and varies from grid point to grid point for example from green for low patient thickness and smoothly merges and transitions via yellow and orange to red for high patient thickness. In the color-coding embodiment, the user is therefore once more alerted to stay clear from those "red" imaging geometries that result in high attenuation levels because of the patient's anatomy. In one embodiment and as shown in FIG. 6 the color-coding or gray-value or line type coding of the grid points 605 extends along the respective 4 neighboring lines whose intersection forms the respective grid point 605 which may be called a "hair cross" style grid point 605. The color-coding along each line gradually transitions into the color of the neighboring grid point.

In other embodiments of FIG. 6 the grid is "tiled" with the grid position indicators 605 being tiles of small squares or rectangles similar to the embodiment of FIG. 3. In other embodiments, when the hair cross grid structure is used, the visual coding is by varying line types such as solid, dashed and dotted used for the grid and the grid points 605.

In one embodiment there is also a dose usage indicator symbols 610*a-c* overlaid on said grid points 605 whose individual size varies with the actual dose usage in a current image acquisition procedure ("exam") or the accumulated dose usage from a previous exam or a series of previous exams. In other words, the size of indicator symbol 610*a*, 610*b* or 610*c* "grows" dynamically and GUI is updated accordingly as more and more dosage is delivered at the respective imaging geometry. In one embodiment it is the grid points 605 themselves that are arranged as dose usage indicator symbols. In one embodiment the dose usage indicator symbols 610*a-c* are arranged as circles but it is understood that other geometric configurations or shapes may also be used such as squares or triangles.

In one embodiment there is also code indicator bar 615 for easy visual translation of the colour or gray value -mapping used for the visual coding into the actual patient thickness measured for example in mm or cm. The color-coding is switchable between different colour-palettes for example by mouse-click on the code indicator bar 615.

In one embodiment, the date underlying the grid's color-coding is derived from historical data acquired over many exams collected and collated from databases from across many different hospitals or medial facilities. In one embodiment the color-coding depicts the average water equivalent patient thickness for the respective angulation and rotation. Alternatively, the colour-palette used for the color-coding may also be mapped to average or peak Air Kerma rates (the amount of kinetic energy that needs be released in a unit mass of air in a certain time interval, a measure of the amount of X-ray radiation per time interval, measured in miliGray per second, mGy/s) or effective dose (measured in Sievert units) where the specific radiation sensitivity of the human anatomy is also taken into account.

As mentioned briefly earlier, the UI controller is configured to vary the size of dose usage indicator symbols 610*a-c* with the usage for the current exam. For example, in the embodiment in FIG. 6, the diameter of symbol 610*a* is the largest so most of the dosage has been delivered at imaging geometry position about $\alpha=30°$, $\beta=-10°$.

In other embodiments symbol 610*a-c* size represents a series of exams of the same type within a definable period, for example all Cardio PCI exams of the last month. In this embodiment, the size of symbols 610*a-c* dose is scaled relative to the respective Air Kerma (AK) units. Alternatively, symbol 610*a-c* size may also be scaled relative to fluoro time (seconds/minutes), the number of runs, or the number of frames in the current and previous exam. In one embodiment, the scaling of said symbol 610*a-c* size is selectable and switchable for example by mouse click on a designated "CONVERT" button (not shown) among those quantities describing the dose usage. The dose usage indicator symbols 610*a-c* may also be used in the FIG. 3 embodiment and it is understood that the above mentioned embodiments as to grid positions 605 and dose usage indicator symbols 610*a-c* are equally applicable to FIG. 3 whose grid structure may be other than the shown tile style.

"Grid structure" and grid points as used herein are to be construed broadly. For example, the grid positions 605 may also refer to individual screen pixels with the grid structure than formed as an array of pixels on the screen. In this embodiment, the GUI 195 includes a rectangle formed by the axis for the imaging geometry positions $\alpha$, $\beta$ the pixels varying their color or gray values across the plane of the rectangle to so indicate the varying patient thickness.

In one embodiment, the GUI 195 allows toggling between different axis units for the imaging geometry to thereby effect a zooming into a "region of interest" in the imaging geometry "landscape" formed by the pair $\alpha$, $\beta$.

In one embodiment of a single exam, the colour-coding or scaling for the gird can also be re-mapped or re-scaled to the specific patient under exam. In this embodiment, the minimum and average thickness in the GUI is made to correspond to the actual minimum and average thickness of the patient currently under examination. It is envisaged that the user is provided with a suitable pop-up window to enter the corresponding physical data of the current patient.

The historical or statistical data on patient thickness underlying the grid color-coding is different for different exam types such as cardiology or neurology. The example in FIG. 6 shows an example from cardiology. In one embodiment the color-coding is switchable between different exam types such as neurology or cardiology. This can be achieved by classifying the statistical patient thickness data according to said exam types in database 205 and retrieving the one that fits the current exam when UI controller operates to build up the GUI. The attenuation level data as used herein such as patient thickness, Kerma, and effective dosage may also be derived after suitable conversion from the stored functional geometry-position-dosage relationship held in database 205 introduced above in relation to FIG. 3.

In one embodiment, the symbol 610*a-c* size for example the circle's diameters is scaled such that the largest circle has maximum size corresponding to the size of the grid. For example the user may choose a setting that the largest circle is not to cover an area more than a certain number of grid squares. The remaining symbols 610*a-c* sizes are than downscaled accordingly relative to said maximum size. This measure allows maintaining good and unobstructed vision on the whole of the grid even when there is preponderance of a certain geometry position in the current exam or across a series of exams.

When GUI 195 is used live during an exam, the current angle of the geometry can be highlighted for ease of navigation.

In one embodiment symbol 610*a-c* may be arranged as interactive GUI widgets so the user can retrieve the actual quantity in which the dose usage is measured. In one embodiment, when user lets a mouse cursor hover over a desired one of symbols 610*a-c*, the GUI controller intercepts this event and effects in response a "tool tip" window to pop-up overlaid on GUI 195 and positioned close to the desired one of the symbol 610*a-c* with said tool tip window including a text string for the respective unit and amount of dosage.

With reference to FIGS. 7A-C, further schematic screenshot of GUI diagrams are shown that may be generated and displayed instead or alongside the GUI embodiments previously described. In one embodiment, the diagram GUIs according to FIGS. 7A-C are used as reporting tools that are generated by default at the conclusion of an exam to summarize dose usage from different aspects. In one embodiment, the GUIs in FIGS. 7A-C may also be used live during an on-going procedure and are updated as the exam progresses. The GUIs as depicted in FIG. 7A-C may be displayed together or separately or in any grouping as desired by the user.

FIG. 7A shows a bar 702 plot of dose usage versus lateral or frontal SID (Source Image Distance) and FIG. 7B shows a bar 706 plot of dose usage versus Source Skin Distance (SSD). SSD is related to the height of exam table 110 used to support the patient during the exam. Alternatively, bar 706 may display the table height. The respective bars 702, 706 are color- or gray-value coded to show the relative dosage at the respective SID or SSD or table height usage. Coding by filling the bars with different patterns or hachures is also envisaged in some embodiments. This is information useful for training purposes.

FIG. 7C shows X-ray dosage usage versus detector size used during the image acquisition procedure or in previous image acquisition procedures. According to one embodiment, the actual portion of the detector 110's radiation sensitive surface used for a given exam run is variable. The detector size used is measured in cm of the diagonal across the used detector size surface. For example "format" FD31 means that detector surface with 31 cm diagonal across has been used. The dosage used for that detector format FD31 is indicated by dosage usage per format bar 708. In one embodiment the imager 100 includes a collimator. If collimation is used to further restrict exposure within the chosen detector format, the bar is shown as spilt into two sub-bars 710b,a, each showing in proportion the fraction of detector usage with or without collimation, respectively. In the example shown in FIG. 7C collimation usage bar 710b shows the average fraction of detector surface that was blocked out by user controlled collimation for the respective detector size or format. Correspondingly, "no-collimation" bar 710a shows the average fraction of detector surface that was not blocked out by user controlled collimation for the respective detector size or format FD15-FD48. In one embodiment, dosage usage bar 708 is displayed in shutter or wedge format. In this embodiment, collimation usage bar 710b is an "overlay" on bar 708 forming a "shutter" with the position of its upper edge relative to the top edge of bar 708 indicating the fraction of collimation usage. So if the collimation usage bar 710b overlay is half the size of bar 708, on average 50% of the area of that respective detector format has been covered by a user controlled collimator. In other embodiments, bars 710a,b or bars 708 and bar 710b have different colour- or gray-shadings or the fraction of used detector size is visually coded by filling the bars with different patterns or hachures. In yet other embodiments, no bar plot is used but other suitable representations such as pie-charts. Coding by different fill patterns is also envisaged for some embodiments of FIG. 3.

In the above embodiments, imager settings data, that is, the collimator settings, table height settings, SID and currently used X-ray dosage may be retrieved by apparatus 200 via suitable interfacing with imager 100 during operation or may be extracted from DICOM or other meta-data included in the acquired projection images. In one embodiment, said data are provided by imager 100 separately from the acquired images as a data stream and committed to a database for each exam. Apparatus 200 can connect to said database to acquire said setting data. The settings data is then passed to GUI controller 210 and then processed to produce the above GUI 195 according to the respective embodiments in FIGS. 3, 4, 6 and 7. For each of the mappings used to effect the visual coding a suitable reference point from one of the grid points is chosen either by the user or is set by default by apparatus 200.

With reference to FIG. 5, a flow chart is shown for a method of aiding operation of x-ray imager 100 during image acquisition.

In a first step S501, a request to change a current imaging geometry position for an updated geometry position is received.

In step S515, memory 205 is accessed, the memory having stored thereon a functional relationship between the imaging geometry positions and the x-ray dosages.

The stored functional relationship is based on expected x-ray attenuation levels in the object of interest. In one embodiment the values making up the functional relationship are acquired earlier and pre-loaded onto the memory unit.

According to another embodiment, the data values are calculated on demand by a suitably programmed numerical routing implementing the functional relationship.

In step S520 the data values retrieved after memory access are used to provide to the human operator of the interventional x-ray imager an indication of the change in x-ray dosage required at the updated imaging geometry position x-ray dosages taken relative to the x-ray dosage required at a reference position among a plurality of imaging geometry positions.

In one embodiment, the indication is updated whenever the current imaging position is incrementally updated.

According to one embodiment the method allows the operator to select the reference position to be the current position or any other of the imaging positions among the plurality of imaging geometry positions.

According to one embodiment providing of the indication includes generating for display on a screen a graphic display the graphic display when displayed including a plurality of geometry position versus x-ray dosage indicator elements.

According to one embodiment the providing of the indication includes generating for display on a screen a graphics display, the graphics display when so displayed including a grid structure with different grid position indicators representative of different imaging geometry positions, the grid position indicators are visually coded with the coding varying across the grid position indicators with the change in required X-ray dosage, said change expressed in terms of the level of X-ray attenuation to be expected when the respective imaging geometry is used for the image acquisition of the object, the graphics display further including at least one dosage usage indicator having a size and positioned at any one of the grid points, the size changing with the X-ray dosage used in a current imaging procedure or in a series of previous imaging procedures at the respective imaging geometry position. According to yet another embodiment providing the indication includes creating an acoustic signal having a pitch in direct variance with the relative change in x-ray dosage requirements as the C arm moves across the plurality of the imaging geometry positions.

According to yet another embodiment the providing of indication includes delivering a negative feedback signal back onto a mechanical control device used by the operator to request the change and to control the imaging geometry positions.

The feedback signal may be provided by a vibration of the joy-stick of the forced feedback type to selectively accelerate/decelerate the speed with which the C arm moves across the various positions.

According to one embodiment the apparatus according to the present invention is formed as an add-on to a collision prevention sub system included in the x-ray imager.

According to one embodiment the functional relationship X-ray dosage versus imaging geometry position is derived in a preparatory phase previous to using the X-ray imager. In the derivation a mathematical and or physical model of various patient physiques are used. In one embodiment, if the imager includes an automatic dosage controller, the same model is used as the one on which the control circuitry of the automatic dosage controller is based.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for aiding operation of an x-ray imager during an image acquisition procedure, the X-ray imager being configured to vary X-ray dosages depending on differences in X-ray attenuation levels across an object of interest to be imaged, the X-ray imager being further configured to assume any one of a plurality of imaging geometry positions when acquiring an image, the apparatus comprising:
    an input unit configured to receive a request to change a current imaging geometry position for an updated imaging geometry position for use in an image acquisition;
    a memory unit configured to store a function relationship between the plurality of imaging geometry position and the X-ray dosages, the function relationship being based on expected X-ray attenuation levels in the object of interest; and
    an output unit configured to use the stored function relationship to provide to an operator of the X-ray imager an indication of a relative change in X-ray dosage required at the updated imaging geometry position relation to the X-ray dosage required at a reference position.

2. The apparatus of claim 1, wherein the indication is visual and displayable on a screen as a graphics display, the graphics display when so displayed comprises the plurality of imaging geometry positions versus X-ray dosage indicator elements, each indicator element representing one imaging geometry position of the plurality of imaging geometry positions and the relative change of X-ray dosage required at the one imaging geometry position.

3. The apparatus of claim 2, wherein the relative change in X-ray dosage is visually-coded by the indicator elements, the visual-coding directly varying with the relative changes in X-ray dosage requirements across the indicator elements.

4. The apparatus of claim 2, wherein the graphics display further comprises at least one dosage usage indicator having a size and positioned at one of the indictor elements, the size changing with the X-ray dosage used in a current image acquisition procedure or the size representing the X-ray dosage used at a respective imaging geometry position in a previous image acquisition procedure or in a series of previous image acquisition procedures.

5. The apparatus of claim 2, wherein the indicator elements form points of one of a plurality of contour lines of the stored functional relationship between the plurality of imaging geometry positions and the X-ray dosages.

6. The apparatus of claim 2, wherein the graphics display is a graphical user interface comprising a cursor, a position of the cursor in the graphics display representative of the current imaging geometry position, the position of the cursor varying as the X-ray imager changes from the current imaging geometry position to the updated imaging geometry position.

7. The apparatus of claim 1, wherein the indication is provided by an acoustical signal having a pitch in direct variance with the relative change in X-ray dosage requirements across the plurality of imaging geometry positions, the pitch varying as the X-ray imager changes from the current imaging geometry position to the updated imaging geometry position.

8. The apparatus of claim 1, wherein the indication is configured to be a haptic indication in a form of a negative feedback signal acting on a mechanical control device used by the operator to request the change in the current imaging geometry position, wherein the haptic indication comprises vibration imparted on the mechanical control device, wherein at least one of a feedback strength of the negation feedback signal and a frequency of the vibrations are in direct variance with the relative change in X-ray dosage requirements at and across the plurality of imaging geometry positions, and wherein at least one of the feedback strength and the frequency of the vibrations varying as the X-ray imager changes from the current imaging geometry position to the updated imaging geometry position.

9. The apparatus of claim 1, wherein the indication is visual and displayable on a screen as a graphics display, the graphics display when so displayed comprising a grid structure with different grid position indicators representative of different imaging geometry positions of the plurality of imaging geometry positions, the different grid position indicators being visually coded, said visual coding varying across the different grid position indicators with the relation change in required X-ray dosage, said relative change expressed in term of the expected X-ray attenuation levels to be expected when a respective imaging geometry position of the plurality of imaging geometry positions is used for the image acquisition of the object of interest, and wherein the graphics display further comprises at least one dosage usage indicator having a size and positioned at one of the different grid position indicators, the size changing with the X-ray dosage used in a current image acquisition procedure or the size representing the X-ray dosage used at the respective imaging geometry position in a previous image acquisition procedure or in a series of previous image acquisition procedures.

10. The apparatus of claim 9, wherein the visual coding comprises one of i) a color coding, ii) a gray-value coding and ii) a coding by using different line types for lines used in defining the grid structure.

11. The apparatus of claim 9, wherein the graphics display further comprises a further dosage usage indicator having a further size, the output unit operative to scale the size and the further size relative to one another so that the larger one of the size and the further size is not to exceed a predefined maximum size, the predefined maximum size being preset in relation to a size of the grid structure displayed on the graphics display.

12. The apparatus of claim 9, wherein a visual-encoding of a level of attenuation of the expected X-ray attenuation levels is by mapping into one of i) average water equivalent patient thickness, ii) average or peak air Kerma rate, and iii) effective dosage for the object of interest.

13. The apparatus of claim 1, wherein the indication is visual and displayable on a screen as a graphics display, the object of interest being disposed on a table during the image acquisition, and wherein the graphics display when so displayed comprises a visually-coded Source-Image-Distance indicator or a visually-coded table height indicator, the visual coding of the Source-Image-Distance indicator and the table height indicator indicating the relative change in X-ray dosage required or used for a respective Source-Image-Distance or table height.

14. The apparatus of claim 1, wherein the indication is visual and displayable on a screen as a graphics display, the graphics display when so displayed comprising a visually-coded indicator for the X-ray dosage used for a user-selectable X-ray detector surface size in the image acquisition procedure and a collimation usage indicator indicating collimator usage for said user-selectable X-ray detector surface size.

15. The apparatus of claim 3, wherein the visual coding comprises one of a color coding and a gray-value coding.

16. The apparatus of claim 1, wherein the X-ray imager is an interventional C-arm.

17. The apparatus of claim 1, wherein each of the plurality of imaging geometry positions is given by a parameter comprising at least one of a rotation angle, an angulation angle and an X-ray source-to-image distance.

18. A method of aiding operation of an X-ray imager during an image acquisition procedure, the X-ray imager being configured to vary X-ray dosages depending on differences in X-ray attenuation levels across an object of interest to be imaged, the X-ray imager being further configured to assume any one of a plurality of imaging geometry positions when acquiring an image, the method comprising acts of:
  receiving a request by an input unit to change a current imaging geometry position for an updated imaging geometry position for use in an image acquisition;
  accessing a memory unit having stored thereon a functional relationship between the plurality of imaging geometry positions and the X-ray dosages, the functional relationship being based on expected X-ray attenuation levels in the object of interest; and
  using the stored functional relationship for providing to an operator of the X-ray imager an indication of a relative change in X-ray dosage required at the updated imaging geometry position relative to the X-ray dosage required at a reference position via an output unit.

19. The method of claim 18, wherein the using act for providing of the indication comprises generating for display on a screen a graphics display, the graphics display when so displayed comprising the plurality of geometry position versus X-ray dosage indicator elements, each indicator element representing one of the plurality of geometry positions and the relative change of X-ray dosage required at the one imaging geometry position.

20. The method of claim 18, wherein the using act for providing of the indication comprises delivering a negative feedback signal, the negation feedback signal acting on a mechanical control device used by the operator to request the change in the current imaging geometry position, the negative feedback signal configured to impart vibrations on the mechanical control device, and wherein a strength of the negative feedback signal or a frequency of the vibrations are in direct variance with the relative change in X-ray dosage requirements at and across the plurality of imaging geometry positions, the negative feedback strength or the frequency of the vibrations being configured to vary as the X-ray imager changes from the current imaging geometry position to the updated imaging geometry position.

21. The method of claim 18, wherein the using act for providing of the indication comprises generating for display on a screen a graphics display, the graphics display when so displayed comprisinq a grid structure with different grid position indicators representative of different imaging geometry positions, the grid position indicators are visually coded with the coding varying across the grid position indicators with the relative change in required X-ray dosage, said relative change being expressed in terms of the expected X-ray attenuation levels to be expected when a respective imaging geometry position is used for the image acquisition of the object, and wherein the graphics display further comprises at least one dosage usage indicator having a size and positioned at one of the grid position indicators, the size changing with the X-ray dosage used in a current image acquisition procedure or in a series of previous image acquisition procedures at the respective imaging geometry position.

22. An X-ray imager including an apparatus for aiding operation of the X-ray imager during an image acquisition procedure, the X-ray imager configured to varying X-ray dosages depending on diffences in X-ray attenuation levels across an object of interest to be imaged, the X-ray imager being further capable of assuming any one of a plurality of imaging geometry positions when acquiring an image, the apparatus comprising:
- an input unit configured to receive a request to change a current imaging geometry position for an updated imaging geometry position for use in an image acquisition;
- a memory unit configured to store a functional relationship between the plurality of imaging geometry positions and the X-ray dosages, the functional relationship being based on expected X-ray attenuation levels in the object of interest; and
- an output unit configured to use the stored functional relationship to provide to an operator of the X-ray imager an indication of a relative change in X-ray dosage required at the updated imaging geometry position relative to the X-ray dosage required at a reference position.

23. A non-transitory computer readable medium comprising computer instruction which, when executed by a processor, configure the processor to perform acts for aiding operation of an X-ray imager during an image acquisition procedure, the X-ray imager being configured to vary X-ray dosages depending on difference in X-ray attenuation levels across an object of interest to be imaged, the X-ray imager further being configured to assume any one of a plurality of imaging geometry position when acquiring an image, the acts comprising:
- receiving a request by an input unit to change a current imaging geometry position for an updated imaging geometry position for use in an image acquisition;
- accessing a memory unit having stored thereon a functional relationship between the plurality of imaging geometry positions and the X-ray dosages, the functional relationship being based on expected X-ray attenuation levels in the object of interest; and
- using the stored functional relationship for providing to an operator of the X-ray imager an indication of a relative change in X-ray dosage required at the updated imaging geometry position relative to the X-ray dosage required at a reference position via an output unit.

* * * * *